(12) United States Patent
Takahashi et al.

(10) Patent No.: US 7,582,363 B2
(45) Date of Patent: Sep. 1, 2009

(54) ORGANIC POLYMER LIGHT-EMITTING ELEMENT MATERIAL HAVING GOLD COMPLEX STRUCTURE AND ORGANIC POLYMER LIGHT-EMITTING ELEMENT

(75) Inventors: Yoshiaki Takahashi, Chiba (JP); Isamu Taguchi, Chiba (JP); Koro Shirane, Chiba (JP)

(73) Assignee: Showa Denko K.K., Tokyo (JP)

( * ) Notice: Subject to any disclaimer, the term of this patent is extended or adjusted under 35 U.S.C. 154(b) by 536 days.

(21) Appl. No.: 10/555,067

(22) PCT Filed: Apr. 28, 2004

(86) PCT No.: PCT/JP2004/006180

§ 371 (c)(1),
(2), (4) Date: Oct. 28, 2005

(87) PCT Pub. No.: WO2004/096947

PCT Pub. Date: Nov. 11, 2004

(65) Prior Publication Data

US 2006/0269779 A1    Nov. 30, 2006

Related U.S. Application Data

(60) Provisional application No. 60/470,187, filed on May 14, 2003.

(30) Foreign Application Priority Data

Apr. 30, 2003    (JP)    ............... 2003-125777

(51) Int. Cl.
 *H01L 51/54*    (2006.01)
 *C09K 11/06*    (2006.01)
(52) U.S. Cl. .......... 428/690; 428/917; 313/504; 313/506; 252/301.18; 257/E51.027; 257/E51.035; 257/E51.044; 528/9; 528/395
(58) Field of Classification Search ............... 428/390, 428/917; 313/504, 506; 257/40, E23.162, 257/E51.044, E51.027, E51.033–E51.037; 556/110; 528/9, 395; 252/301.18
See application file for complete search history.

(56) References Cited

U.S. PATENT DOCUMENTS

2002/0045062 A1 *    4/2002    Senoo et al. ............... 428/690
2002/0193532 A1 *    12/2002    Ikehira et al. ............ 525/333.3

FOREIGN PATENT DOCUMENTS

EP    1 245 659 A1    10/2002

OTHER PUBLICATIONS

Puddephatt, R. J. "Precious metal polymers: platinum or gold atoms in the backbone." Chemical Communications. 1998, pp. 1055-1062.*
Yam et al. "Synthesis characterization, structure and luminescence studies of mono-, di-, and trinuclear gold(I) phosphine alkynyl complexes." Journal of Organometallic Chemistry. 2003, vol. 381, pp. 196-209.*
Dana Eisler, et al, "An Organometallic Octopus Complex: Structure and Properties of a Resorcinarene with 16 Cobalt Centers" Organometallics, vol. 21, 2002, pp. 3955-3960, XP002290460.
Wei Lu, et al, "The $^3(\pi\pi^*)$ Emission of $Cy_3PAu(C\equiv C)_nAuPCy_3$ (n=3, 4). Effect of Chain Length Upon Acetylenic $^3(\pi\pi^*)$ Emission" Organometallics, vol. 21, Mar. 5, 2002, pp. 2343-2346, XP002272313.
Nicholas C. Payne, et al, "Easy Double Metalation of a Diphosphinomethane Ligand: Structure of the Remarkable Octagold Cage Complex $[Au_8Cl_2\{\mu_3-(MeO)_2PCHP(OMe)_2\}_s\}_s-\{\mu_4-(MeO)_2PCP(OMe)_2\}_2]CHCl_3$," Organometallics, vol. 9, 1990, pp. 880-882, XP002290461.
Ratnavathany Narayansaswamy, et al, "Synthesis, Structure, and Electronic Spectroscopy of Neutral, Dinuclear Gold(I) Complexes. Gold(I)—Gold(I) Interactions in Solution and in the Solid State", Inorganic Chemistry, American Chemical Society, vol. 32, 1993, pp. 2506-2517, XP002280188.
Michael J. Irwin, et al, "Rigid-Rod Polymers and Model Compounds with Gold(I) Centers Bridged by Diisocyanides and Diacetylides", Organometallics, vol. 15, 1996, pp. 51-57, XP002290462.
Michael J. Irwin, et al, "Luminescent Gold(I) Acetylides: From Model Compounds to Polymers", Organometallics, vol. 16, 1997, pp. 3541-3547, XP002290463.

* cited by examiner

*Primary Examiner*—D. Lawrence Tarazano
*Assistant Examiner*—Michael Wilson
(74) *Attorney, Agent, or Firm*—Sughrue Mion, PLLC (57) ABSTRACT

The present invention provides an organic polymer light-emitting element material having a gold complex structure as a part of the side chain or crosslinking group as represented by formulae (5) and (8) and an organic polymer light-emitting element comprising layer(s) comprising the organic polymer light-emitting element material. The present invention provides a polymer-based phosphorescent material useful for a multicolor or white light-emitting organic EL device having high luminous efficiency and capable of large-area formation and mass production.

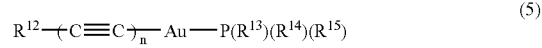

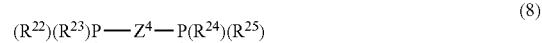
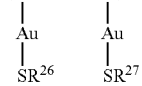

3 Claims, 1 Drawing Sheet

FIG. 1

ORGANIC POLYMER LIGHT-EMITTING ELEMENT MATERIAL HAVING GOLD COMPLEX STRUCTURE AND ORGANIC POLYMER LIGHT-EMITTING ELEMENT

CROSS-REFERENCE TO RELATED APPLICATION

This is an application pursuant to 35 U.S.C. Section 111(a) with claiming the benefit of U.S. Provisional application Ser. No. 60/470,187 filed May 14, 2003 under the provision of 35 U.S.C. Section 111(b), pursuant to 35 U.S.C. Section 119(e) (1).

TECHNICAL FIELD

The present invention relates to a polymer-based organic light-emitting element material for use in an organic light-emitting device (OLED) which can emit light by an electric energy and be used for a flat display panel, a backlight or illumination light source used in the flat display panel, an electronic photograph, a photo-device light source, a display board or the like.

BACKGROUND ART

Since an organic light-emitting device capable of high brightness light emission was invented by C. W. Tang et al. of Kodak in 1987 (see, *Appl. Phys. Lett.*, Vol. 51, page 913 (1987)), the development of materials therefor and improvement of the device structure are abruptly proceeding and its practical use in a display for car audio, cellular phone and the like has been started in recent years. In order to further expand applications of this organic EL (electroluminescence), studies are being aggressively made to develop materials for enhancing the luminous efficiency or durability or to develop full-color display.

As for the luminous efficiency, since the ratio of exciton produced in the electrical excitation between the singlet excited state and the triplet excited state is 1:3, the internal quantum efficiency in light emission of an organic EL using, as the light-emitting material, a fluorescent material which emits from singlet excited state has an upper limit of 25% (see, *Gekkan Display* (*Monthly Display*), separate volume "Organic EL Display", page 58 (October, 1998)). On the other hand, when a phosphorescent material emitting from triplet excited state is used as the light-emitting material, the produced singlet excited state and triplet excited state both contribute to the light emission and therefore, the upper limit of internal quantum efficiency is 100%.

Many of phosphorescent materials are a compound containing a heavy metal atom. Y. Ma et al. disclose an organic EL device using, as the light-emitting material, a coordination compound having gold as the center metal (see, *Adv. Mater.*, Vol. 11, page 852 (1999)). Thereafter, V. W.-W. Yam et al. have also taken notice of good phosphorescent emission property of the gold complex and use it as the light-emitting material of an organic EL device (see, *Chem. Commun.*, page 53 (2000)).

For production of an organic EL device, a vacuum vapor deposition method has been conventionally used. However, this method has problems in that vacuum equipment is necessary and that the larger the area of the device is, the more difficult it is to form an organic thin film having a uniform thickness. On the other hand, an inkjet method and a printing method, which are being developed as a technique of forming the film by coating, can form a film under atmospheric pressure and moreover, ensure excellent performance in the large-area formation or mass production of the device. In the film formation by these methods, a low molecular weight compound having possibility of causing phase separation or segregation cannot be used and therefore, a polymer light-emitting material of undergoing no crystallization must be used.

However, most compounds heretofore known as a polymer containing a gold complex have a structure such that gold is contained in the polymer main chain (see, *Chem. Commun.*, page 1055 (1998)). Such a structure is defective in that the gold concentration in the polymer can be hardly controlled, that a multifunctional polymer having a light-emitting moiety and an electron transport moiety or the like can be hardly obtained, or that the molecule decomposes by dissociation of bond between gold and an organic group. Therefore, light-emitting material of an organic EL device is required to be a compound having a polymer main chain constituted only by an organic group.

As for the color of emitted light, studies are being aggressively made in recent years to develop a full color display or a white light source by utilizing an organic EL device and under these circumstances, the problem to be solved is to develop, among phosphorescent materials having a high luminous efficiency, a multi-color light-emitting material including blue light emission having a short wavelength.

In this way, for producing a large-area colored/white organic EL device having high luminous efficiency, development of a polymer material facilitated in the control of light emission color and containing a phosphorescent emission moiety is being demanded.

DISCLOSURE OF INVENTION

An object of the present invention is to provide a polymer-based phosphorescent material useful for a multicolor or white light-emitting organic EL device having high luminous efficiency and capable of large-area formation and mass production.

The present inventors have accomplished the present invention by using a polymer material which is a phosphorescent coordination compound having a gold complex structure (phosphorescent gold complex).

That is, the present invention relates to the following organic polymer light-emitting element material and an organic polymer light-emitting element using the organic polymer light-emitting element material.

1. An organic polymer light-emitting element material having a gold complex structure as a part of the side chain or crosslinking group.
2. The organic polymer light-emitting element material as described in 1 above, wherein the molecular weight of the organic polymer is from 1,000 to 1,000,000.
3. The organic polymer light-emitting element material as described in 1 or 2 above, which is obtained by polymerizing a composition containing a polymerizable gold complex where at least one ligand has a polymerizable functional group as the substituent.
4. The organic polymer light-emitting element material as described in 1 above, wherein the gold complex structure has an organic phosphine compound as at least one ligand.
5. The organic polymer light-emitting element material as described in 3 above, wherein at least one ligand of the polymerizable gold complex is an organic phosphine compound.
6. The organic polymer light-emitting element material as described in 5 above, wherein at least one organic phosphine compound as the ligand has a polymerizable functional group as the substituent.

7. The organic polymer light-emitting element material as described in any one of 4 to 6 above, wherein the organic phosphine compound is represented by formula (1):

$$P(R^1)(R^2)(R^3) \quad (1)$$

wherein $R^1$ to $R^3$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent.

8. The organic polymer light-emitting element material as described in any one of 4 to 6 above, wherein the organic phosphine compound is represented by formula (2):

$$(R^4)(R^5)P\text{-}Z^1\text{-}P(R^6)(R^7) \quad (2)$$

wherein $R^4$ to $R^7$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, and $Z^1$ represents an organic group which crosslinks two phosphorus atoms, such as alkylene group having 1 to 20 carbon atoms which may have a substituent, alkylene group having 3 to 15 carbon atoms which has a cyclic structure and which may have a substituent, or arylene group having 6 to 20 carbon atoms which may have a substituent.

9. The organic polymer light-emitting element material as described in any one of 3 to 6 above, wherein the polymerizable gold complex has a structure represented by formula (3):

wherein $R^4$ to $R^7$ and Z1 have the same meanings as in 8 above, $R^8$ to $R^{11}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, $Z^2$ represents an organic group which crosslinks two phosphorus atoms, such as alkylene group having 1 to 20 carbon atoms which may have a substituent, alkylene group having 3 to 15 carbon atoms which has a cyclic structure and which may have a substituent, or arylene group having 6 to 20 carbon atoms which may have a substituent, and $A^-$ represents a monovalent anion, provided that at least one of $R^4$ to $R^{11}$, $Z^1$ and $Z^2$ has a polymerizable functional group.

10. The organic polymer light-emitting element material as described in any one of 3 to 6 above, wherein the polymerizable gold complex has a structure represented by formula (4):

wherein $R^4$ to $R^7$ and $Z^1$ have the same meanings as in 8, and Hal represents a halogen atom, provided that at least one of $R^4$ to $R^7$ and $Z^1$ has a polymerizable functional group.

11. The organic polymer light-emitting element material as described in any one of 1 to 4 above, wherein the gold complex structure has at least one alkynyl ligand.

12. The organic polymer light-emitting element material as described in any one of 3 to 6 above, wherein the polymerizable gold complex has a structure represented by formula (5):

$$R^{12}\text{---}(C\equiv C)_n\text{---}Au\text{---}P(R^{13})(R^{14})(R^{15}) \quad (5)$$

wherein $R^{12}$ represents a hydrogen atom, a cyano group, a silyl group having 3 to 20 carbon atoms, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an aryl group having 6 to 15 carbon atoms which may have a substituent, a heteroaryl group having 3 to 15 carbon atoms which may have a substituent, an acyl group having 1 to 15 carbon atoms, a carboxyl group, or an alkoxy carbonyl group having 2 to 15 carbon atoms, $R^{13}$ to $R^{15}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, and n represents an integer of 1 to 5, provided that at least one of $R^{12}$ to $R^{15}$ has a polymerizable functional group.

13. The organic polymer light-emitting element material as described in any one of 3 to 6 above, wherein the polymerizable gold complex has a structure represented by formula (6):

(6)

wherein $R^{16}$ to $R^{19}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, $R^{20}$ to $R^{21}$ each independently represents a hydrogen atom, a cyano group, a silyl group having 3 to 20 carbon atoms, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an aryl group having 6 to 15 carbon atoms which may have a substituent, a heteroaryl group having 3 to 15 carbon atoms which may have a substituent, an acyl group having 1 to 15 carbon atoms, a carboxyl group, or an alkoxy carbonyl group having 2 to 15 carbon atoms, $R^{20}$ and $R^{21}$ may be linked with each other via a crosslinking group, $Z^3$ represents an organic group which crosslinks two phosphorus atoms, such as alkylene group having 1 to 20 carbon atoms which may have a substituent, alkylene group having 3 to 15 carbon atoms which has a cyclic structure and which may have a substituent, or arylene group having 6 to 20 carbon atoms which may have a substituent, and n represents an integer of 1 to 5, provided that at least one of $R^{16}$ to $R^{21}$ and $Z^3$ has a polymerizable functional group.

14. The organic polymer light-emitting element material as described in any one of 3, 5 and 6 above, wherein the polymerizable gold complex has a structure represented by formula (7):

(7)

wherein $L^1$ and $L^2$ each represents a monodentate or bidentate ligand, at least one of $L^1$ and $L^2$ is the organic phosphine compound described in 7 or 8 above, and n represents an integer of 1 to 5.

15. The organic polymer light-emitting element material as described in any one of 3 to 6 above, wherein the polymerizable gold complex has at least one thiolato ligand.

16. The organic polymer light-emitting element material as described in any one of 3 to 6 above, wherein the polymerizable gold complex has a structure represented by formula (8):

(8)

wherein $R^{22}$ to $R^{25}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, $R^{26}$ and $R^{27}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an aryl group having 6 to 15 carbon atoms which may have a substituent, or a heteroaryl group having 3 to 15 carbon atoms which may have a substituent, and $R^{26}$ and $R^{27}$ may be linked with each other via a crosslinking group, $Z^4$ represents an organic group which crosslinks two phosphorus atoms, such as alkylene group having 1 to 20 carbon atoms which may have a substituent, alkylene group having 3 to 15 carbon atoms which has a cyclic structure and which may have a substituent, or arylene group having 6 to 20 carbon atoms which may have a substituent, provided that at least one of $R^{22}$ to $R^{27}$ and $Z^4$ has a polymerizable functional group.

17. The organic polymer light-emitting element material as described in any one of 3 to 6 above, wherein the polymerizable functional group has radical polymerizability.

18. The organic polymer light-emitting element material as described in any one of 3 to 6 above, wherein the polymerizable functional group is an organic group having a carbon-carbon double bond.

19. An organic polymer light-emitting element comprising a pair of electrodes having interposed therebetween at least one layer comprising the organic polymer light-emitting element material described in any one of 1 to 18 above.

20. An organic polymer light-emitting element comprising a pair of electrodes having interposed therebetween at least one layer each comprising one or more organic polymer light-emitting element material described in any one of 1 to 18 above.

The present invention is specifically described below.

The organic light-emitting element material for use in the organic light-emitting element of the present invention is a coordination compound having gold as the center element, that is, a polymer having a gold complex structure in the side chain or crosslinking group moiety. The polymer light-emitting element material of the present invention may be used singly or may be used as a composite material of this material and a material not containing a gold complex.

In the present invention, the polymer material having a gold complex structure is preferably synthesized by homopolymerizing a polymerizable gold complex having a polymerizable functional group as the substituent or copolymerizing it with a compound other than a polymerizable gold complex, but may also be produced by afterward introducing gold into a polymer having an organic group coordinatable to gold.

The atomic valence of gold in the gold complex structure is not particularly limited but the gold preferably has a valence number of 1 to 4, more preferably 1 and 3. The gold complex may be an ionic complex having an electric charge on the center metal. In this case, a counter ion for neutralizing the electric charge is present.

The polymerizable functional group in the polymerizable gold complex for use in the synthesis of the polymer material of the present invention may be radical polymerizable, anionic polymerizable, addition polymerizable or condensation polymerizable, but a radical polymerizable functional group is preferred. This polymerizable functional group is preferably a group having a carbon-carbon double bond and examples thereof include substituents having an alkenyl group such as vinyl group and allyl group, an alkenoyloxy group such as acryloyloxy group and methacryloyloxy group, a (meth)acryloyloxyalkylcarbamate group such as methacryloyloxyethylcarbamate group, a styryl group or a derivative thereof, or a vinylamide group or a derivative thereof. Among these polymerizable functional groups, in view of polymerizability, a styryl group, an acryloyloxy group, a methacryloyloxy group and a (meth)acryloyloxyalkylcarbamate group are preferred.

The metal complex structure and polymerizable metal complex for use in the present invention preferably contain, as the ligand, at least one organic phosphine compound represented by the following formula (1) or (2):

(1)

(2)

$R^1$ to $R^7$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent.

Examples of alkyl group having 1 to 15 carbon atoms include methyl, ethyl, propyl, isopropyl, butyl, isobutyl, tertiary butyl, amyl and hexyl. Examples of substituent of the alkyl group include aryl groups such as phenyl, tolyl and styryl, alkoxy groups having 1 to 8 carbon atoms such as methoxy and ethoxy, halogen atom, hydroxyl group, nitro group and amino group.

Examples of alkyl group having 3 to 15 carbon atoms which has a cyclic structure include cycloalkyl, cycloalkyl substituted by alkyl, cycloalkyl substituted by cycloalkyl and alkyl substituted by cycloalkyl. The term "cycloalkyl" used herein refers to not only monocyclic one but also polycyclic one such as bicyclic or tricyclic. Polycyclic includes spiro type and bridged type. Specific examples of the alkyl group having a cyclic structure include cyclopentyl, cyclohexyl, perhydronaphtyl, perhydroanthracenyl, cyclohexyl substituted by alkyl group having 1 to 4 carbon atoms and bicyclohexyl. Examples of substituent of these group include aryl groups such as phenyl, tolyl and styryl, alkoxy groups having 1 to 8 carbon atoms such as methoxy and ethoxy, halogen atom, hydroxyl group, nitro group and amino group.

Examples of alkenyl group having 2 to 15 carbon atoms include vinyl, aryl, isopropenyl, butenyl, pentenyl, hexenyl, heptenyl and octenyl. Examples of substituent of the alkenyl group include aryl groups such as phenyl, tolyl and styryl, alkoxy groups having 1 to 8 carbon atoms such as methoxy and ethoxy, halogen atom, hydroxyl group, nitro group and amino group.

Examples of alkoxy group having 1 to 15 carbon atoms include methoxy, ethoxy, propoxy, isopropoxy, buthoxy, isobuthoxy and tertiary buthoxy. Examples of substituent o the alkoxy group include aryl groups such as phenyl, tolyl and styryl, alkoxy groups having 1 to 8 carbon atoms such as methoxy and ethoxy, halogen atom, hydroxyl group, nitro group and amino group.

Examples of aryl group having 6 to 15 carbon atoms include phenyl, naphtyl and anthracenyl. Examples of substituent of the aryl group include alkyl group having 1 to 8 carbon atoms such as methyl and ethyl, alkenyl groups having 1 to 8 carbon atoms such as vinyl, allyl and isopropenyl, alkoxy groups having 1 to 8 carbon atoms such as methoxy and ethoxy, aryl groups such as phenyl, tolyl and styryl, halogen atom, hydroxyl group, nitro group and amino group.

Heteroaryl group having 3 to 15 carbon atoms is a mono-, bi- or tri-cyclic group containing 1 to 4 hetero atoms selected from a group consisting of nitrogen, oxygen and sulfur. Examples thereof include pyridyl, pyrrolyl, imidazolyl, quinolyl, isoquinolyl, thienyl, benzothienyl and furyl. Examples of substituent of the heteroaryl group include alkyl group having 1 to 8 carbon atoms such as methyl and ethyl, alkenyl groups having 1 to 8 carbon atoms such as vinyl, allyl and isopropenyl, alkoxy groups having 1 to 8 carbon atoms such as methoxy and ethoxy, aryl groups such as phenyl, tolyl and styryl, halogen atom, hydroxyl group, nitro group and amino group.

Examples of aryloxy group having 6 to 15 carbon atoms include phenyloxy, naphtyloxy and anthracenyloxy. Examples of substituent of the aryloxy group include alkyl groups having 1 to 8 carbon atoms such as methyl and ethyl, alkenyl groups having 1 to 8 carbon atoms such as vinyl, allyl and isopropenyl, alkoxy groups having 1 to 8 carbon atoms such as methoxy and ethoxy, aryl groups such as phenyl, tolyl and styryl, halogen atom, hydroxyl group, nitro group and amino group.

Among these, alkyl group having 1 to 12 carbon atoms which may have a substituent, aryl group having 4 to 10 carbon atoms which may have a substituent, alkoxy group having 1 to 10 carbon atoms which may have a substituent, and aryloxy group having 4 to 10 carbon atoms which may have a substituent are preferred, and alkyl group having 1 to 12 carbon atoms which may have a substituent and aryl group having 6 to 10 carbon atoms which may have a substituent are more preferred.

$Z^1$ represents an organic group which crosslinks two phosphorus atoms, such as alkylene group having 1 to 20 carbon atoms which may have a substituent, alkylene group having 3 to 15 carbon atoms which has a cyclic structure and which may have a substituent, or arylene group having 6 to 20 carbon atoms which may have a substituent.

Examples of alkylene group having 1 to 20 carbon atoms include methylene, ethylene, propylene, butylene and hexylene. Examples of substituent of the alkylene group include aryl groups such as phenyl, tolyl and styryl, alkoxy groups having 1 to 8 carbon atoms such as methoxy and ethoxy, halogen atom, hydroxyl group, nitro group and amino group.

Examples of alkylene group having 3 to 15 carbon atoms which has a cyclic structure include cycloalkylene, cycloalkylene substituted by cycloalkyl, alkylene substituted by cycloalkyl, cycloalkylene-cycloalkylene group and alkylene-cycloalkylene group. Here, the term "cyclo-alkylene group" means bicyclic or tricyclic group as well as monocyclic group. Examples thereof include cyclopentylene, cyclohexylene, perhydronaphthylene and perhydro-anthracenylene, cyclohexylene substituted by alkyl group having 1 to 4 carbon atoms, bicyclohexane-diyl and methylene-cyclohexylene. Examples of substituent of these group include aryl groups such as phenyl, tolyl and styryl, alkoxy groups having 1 to 8 carbon atoms such as methoxy and ethoxy, halogen atom, hydroxyl group, nitro group and amino group.

Examples of arylene group having 6 to 20 carbon atoms include o-phenylene, naphtylene, binaphtylene and ferrocenylene. Examples of substituent of the arylene group include alkyl group having 1 to 8 carbon atoms such as methyl and ethyl, alkenyl groups having 1 to 8 carbon atoms such as vinyl, allyl and isopropenyl, alkoxy groups having 1 to 8 carbon atoms such as methoxy and ethoxy, aryl groups such as phenyl, tolyl and styryl, halogen atom, hydroxyl group, nitro group and amino group.

$Z^1$ is preferably an alkylene group having 1 to 4 carbon atoms which may have a substituent, an arylene group having 6 to 20 carbon atoms which may have a substituent or a methylene group which may have a substituent, more preferably an ethylene group which may have a substituent or an o-phenylene group which may have a substituent.

In a case where organic phosphine compound represented by formula (1) is contained as a ligand in the polymerizable gold complex in the present invention, any one of $R^1$ to $R^3$ may be a group containing a polymerizable functional group. In a case where organic phosphine compound represented by formula (2) is contained as a ligand in the polymerizable gold complex in the present invention, any one of $R^4$ to $R^7$ and $Z^1$ may be a group containing a polymerizable functional group.

In a case where any of $R^1$ to $R^7$ contains a polymerizable functional group, the group is an alkenyl group having 2 to 15 carbon atoms which may have a substituent, or an alkyl, alkoxy, aryl or the like group which has a substituent containing a polymerizable functional group. In a case where $Z^1$ contains a polymerizable functional group, $Z^1$ is an alkylene, arylene or the like group which has a substituent containing a polymerizable functional group. Preferable examples of substituent containing a polymerizable functional group include alkenyl groups such as vinyl and allyl, alkenyl-substituted aryl groups such as vinylphenyl, an alkenyl-substituted aralkyl groups such as vinylbenzyl and the like group having a carbon-carbon double bond.

In the present invention, the polymerizable metal complex having a ligand containing a polymerizable functional group as the substituent is preferably used at the time of producing a polymer for an organic light-emitting element material. The "ligand" as used herein is a group comprising an organic compound having from 1 to 40 carbon atoms and having a moiety coordinatable to gold and represents an anionic group such as alkyl group, alkynyl group, aryl group, aralkyl group, heteroaryl group, alkoxy group, aryloxy group, alkylthio group, arylthio group, carboxylate group and dithiocarbamate group, a neutral group such as alkylphosphine, arylphosphine, alkylphosphite, arylphosphite, pyridine, nitrile and isocyanide, or an anionic or neutral chelating compound such as pyridylphenyl group, Schiff base, diketonate and bipyridine. The "anionic" and "neutral" as used herein mean that the formal electric charge of the group bonded to gold is −1 and 0, respectively.

Representative structures of the polymerizable gold complex are the structures of the following formulae (3) to (8):

The substituents $R^4$ to $R^{11}$, $R^{13}$ to $R^{19}$ and $R^{22}$ to $R^{25}$ in these formulae have the same meanings as in the above-described definition of $R^1$ to $R^3$.

$R^{12}$, $R^{20}$ and $R^{21}$ each independently represents a hydrogen atom, a cyano group, a silyl group having 3 to 20 carbon atoms, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an aryl group having 6 to 15 carbon atoms which may have a substituent, a heteroaryl group having 3 to 15 carbon atoms which may have a substituent, an acyl group having 1 to 15 carbon atoms, a carboxyl group, or an alkoxy carbonyl group having 2 to 15 carbon atoms, and $R^{20}$ and $R^{21}$ may be linked with each other via a crosslinking group.

Examples of silyl group having 3 to 20 carbon atoms include trimethylsilyl, triethylsilyl and triphenylsilyl.

Examples of acyl group having 1 to 15 carbon atoms include formyl and acetyl.

Examples of alkoxycarbonyl group having 2 to 15 carbon atoms include methoxycarbonyl, ethoxycarbonyl and 2-ethylhexyloxycarbonyl.

Examples of alkyl group having 1 to 15 carbon atoms which may have a substituent, alkyl group having 3 to 15 carbon atoms which has a cyclic structure and which may have a substituent, alkenyl group having 2 to 15 carbon atoms which may have a substituent, aryl group having 6 to 15 carbon atoms which may have a substituent, heteroaryl group having 3 to 15 carbon atoms which may have a substituent and acyl group having 1 to 15 carbon atoms which may have a substituent, represented by $R^{12}$, $R^{20}$ and $R^{21}$ are the same as above described recitation of $R^1$ to $R^3$.

Among these, an alkyl group having 1 to 10 carbon atoms which may have a substituent, an aryl group having 4 to 10 carbon atoms which may have a substituent, an acyl group having 1 to 10 carbon atoms which may have a substituent, a carboxyl group and an alkoxycarbonyl group having 2 to 10 carbon atoms are preferred, and more preferred are an alkyl group having 1 to 6 carbon atoms which may have a substituent, an aryl group having 6 to 10 carbon atoms which may have a substituent and an alkoxycarbonyl group having 2 to 10 carbon atoms.

Examples of crosslinking group as represented by $R^{20}$ and $R^{21}$ are the same as recited for $Z^1$. Among those examples, preferred are an alkylene group having 1 to 4 carbon atoms and an arylene group having 6 to 20 carbon atoms, and particularly preferred are a propylene group, a butylene group and a naphtylene group.

$R^{26}$ and $R^{27}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an aryl group having 6 to 15 carbon atoms which may have a substituent, or a heteroaryl group having 3 to 15 carbon atoms which may have a substituent, and $R^{26}$ and $R^{27}$ may be linked with each other via a crosslinking group.

Examples of groups as represented by $R^{26}$ and $R^{27}$ are the same as recited for $R^1$ to $R^3$. Examples of crosslinking groups as represented by $R^{26}$ and $R^{27}$ are the same as recited for $R^{20}$ and $R^{21}$.

$Z^2$ to $Z^4$ each independently has the same meaning as $Z^1$.

In formula (4), Hal represents a halogen atom, preferably chlorine, bromine or iodine.

In formulae (5) to (7), n is a parameter greatly contributing to the emission color of phosphorescence and represents an integer of 1 to 5, preferably 1 to 4.

In formula (7), at least one of $L^1$ and $L^2$ is an organic phosphine compound represented by formula (1) or (2), preferably a monodentate or bidentate ligand which is an organic phosphine compound having a polymerizable functional group. The ligand other than the organic phosphine compound is not particularly limited as long as it can form a complex with gold, and examples thereof include an organic nitrogen-containing ligand (e.g., amine ligand, pyridine ligand, nitrile ligand, phenylpyridine ligand, Schiff base), an alkyl ligand, an alkynyl ligand, a carbonyl ligand, a cyanide ligand, an isocyanide ligand, a diketonate ligand, a carboxylate ligand and a dithiocarbamate ligand.

The ligand L is preferably an organic phosphine compound, more preferably trialkylphosphine, triaryl-phosphine, trialkylphosphite or triarylphosphite.

In formula (3), $A^-$ represents a monovalent anion and examples thereof include halide ion, carboxylate ion, sulfonate ion, tetrafluoroborate ion, hexafluorophosphate ion and perchlorate ion. Also, an anion having a valence number of 2 or more, such as carbonate ion, sulfate ion and phosphate ion, may be present in a ratio of neutralizing the electric charge of the gold complex.

Polymerizable gold complex as represented by formulae (3) to (8) contains at least one polymerizable functional group in its structure. In a case where any group of $R^4$ to $R^{26}$ contains a polymerizable functional group, the group is an alkenyl group having 2 to 15 carbon atoms which may have a substituent, or a group which has a substituent containing a polymerizable functional group. In a case where any group of $Z^1$ to $Z^4$ contains a polymerizable functional group, the group is a group which has a substituent containing a polymerizable functional group. Preferred examples of substituent containing a polymerizable functional group include groups having a carbon-carbon double bond such as vinyl, allyl, vinylphenyl and vinylbenzyl.

The polymerizable gold complex for use in the present invention can be synthesized by coordinating a ligand having a polymerizable functional group to gold or by coordinating a ligand having a reactive substituent to gold and reacting the obtained gold complex with a compound having a polymerizable functional group. In this case, examples of the reactive substituent include, but are not limited to, a halogenated alkyl group, a hydroxyl group, a mercapto group, an amino group and a carboxyl group. Examples of the compound having a polymerizable functional group, which is reacted with the reactive substituent group, include, but are not limited to, a polymerizable isocyanate, a polymerizable alcohol and a polymerizable alkoxide.

The mononuclear and polynuclear gold complexes having a polymerizable functional group for use in the present invention each can be produced by the method shown in Scheme 1 below. In the production of either gold complex, gold is reduced by using sodium chloroaurate dihydrate as the starting material. In the reduction, thiodiglycol or the like is used as the reducing agent but in the case of synthesizing a mononuclear gold complex, the organic phosphine compound as the ligand can be made to serve also as the reducing agent. Subsequently, an organic phosphine compound is allowed to act on the produced intermediate, whereby a mononuclear or polynuclear gold chloride complex (I) or (II) is obtained. Furthermore, the chlorine in the obtained gold complex is replaced by a ligand L selected from an organic phosphine compound, acetylide and thiolato, as a result, a complex (III) or (IV) is obtained.

When the polymerizable complex of the present invention has radical polymerizability, the polymerization can be easily performed by using a thermal polymerization initiator such as 2,2'-azobis(isobutyronitrile) (AIBN) and benzoyl peroxide, or an ultraviolet polymerization initiator such as benzophenone, to provide a polymer containing a gold complex moiety.

The polymer may be a homopolymer of the polymerizable gold complex, a copolymer of two or more of the polymerizable gold complexes of the present invention, or a copolymer of one or more of the polymerizable gold complex and one or more polymerizable compound except for the polymerizable gold complex of the present invention. Examples of the polymerizable compound except for the above-described polymerizable gold complex include, but are not limited to, hole-transporting compounds such as vinylcarbazole, electron-transporting compounds such as oxadiazole or triazole derivative having a polymerizable functional group, and compounds not having a carrier-transporting property, such as (meth)acrylic acid alkyl ester (e.g., methyl acrylate, methyl methacrylate), styrene and derivative thereof.

Gold concentration in polymer can be controlled arbitrally by preparing the polymer as a copolymer of one or more kinds of polymerizable gold complexes and one or more kinds of other polymerizable compounds. Gold concentration is not limited and may be determined based on the purpose. When the polymer is used as light-emitting material, it is preferable that the content of gold be 0.01 to 5 mass %. When the polymer is a copolymer, it is preferable that a copolymerization ratio of the polymerizable gold complex be 0.1 to 10 mol %.

Figure 1:
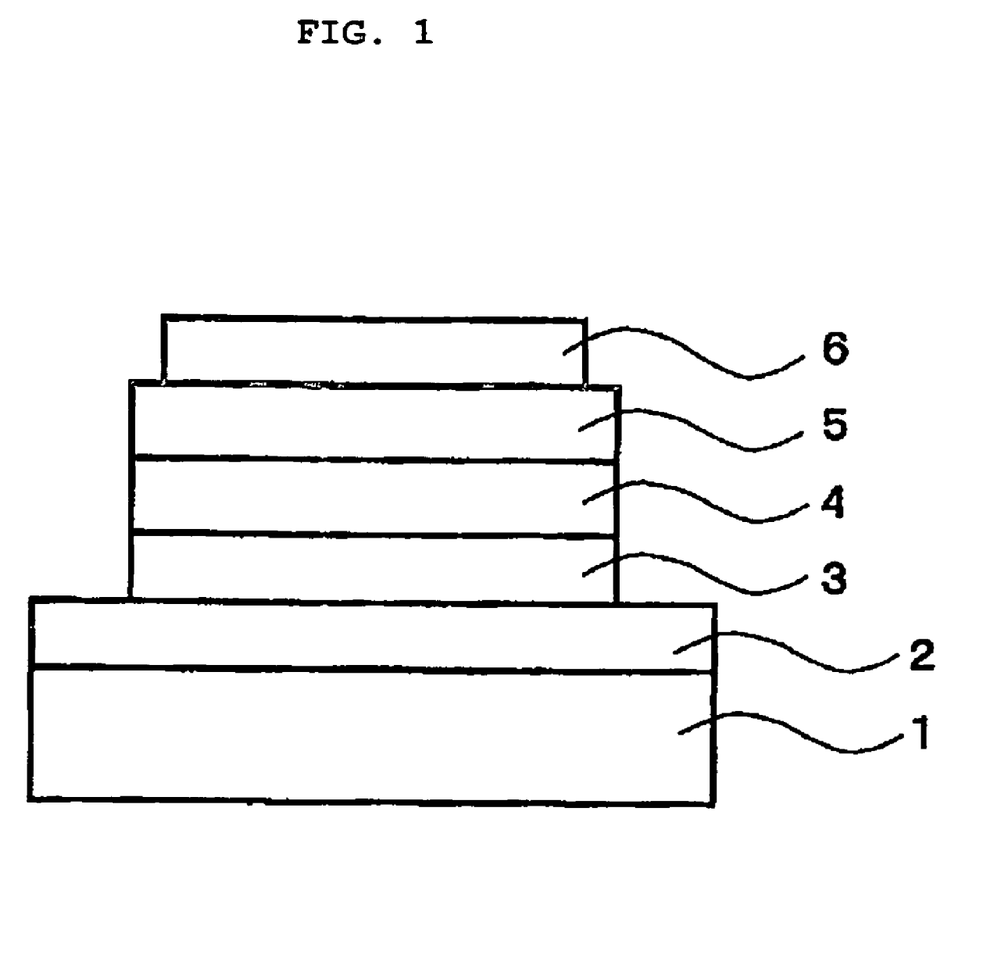
FIG. 1 is an example of cross-sectional view of the organic polymer light-emitting device according to the present invention.

FIG. 1 is a cross-sectional view showing one example of the organic light-emitting element structure according to the present invention, where a hole transport layer 3, a light-emitting layer 4 and an electron transport layer 5 are sequentially formed between the anode 2 and the cathode 6 provided on a transparent substrate 1. The structure of the organic light-emitting element of the present invention is not limited only to the structure shown in FIG. 1, but either 1) a hole transport layer/a light-emitting layer or 2) a light-emitting layer/an electron transport layer may be sequentially provided between the anode and the cathode, or any one layer of 3) a layer containing a hole transport material, a light-emitting material and an electron transport material, 4) a layer containing a hole transport material and a light-emitting material, 5) a layer containing a light-emitting material and an electron transport material, and 6) a light-emitting layer alone may be provided. Furthermore, the light-emitting layer is not limited only to the single layer shown in FIG. 1, but two or more layers may be stacked.

In the case of forming the light-emitting layer of an organic light-emitting element from the light-emitting element material of the present invention, the polymer light-emitting element material may be coated or a polymerizable composition containing the polymerizable gold complex of the present invention may be coated on an underlayer and then polymerized. In the case of coating, the light-emitting element material may be dissolved in an appropriate solvent and coated and thereafter, the solvent may be dried.

The light-emitting layer of the organic light-emitting element of the present invention is a layer containing the polymer light-emitting element material of the present invention as the light-emitting material but may also contain other light-emitting materials, a hole transport material, an electron transport material and the like.

In the organic light-emitting element of the present invention, by forming a hole transport layer and an electron transport layer on both or one side(s) of the light-emitting layer, the luminous efficiency and/or durability can be more improved.

The hole transport material constituting the hole transport layer is not particularly limited, but known hole transport materials can be used, such as TPD (N,N'-dimethyl-N,N'-(3-methylphenyl)-1,1'-biphenyl-4,4'-diamine), α-NPD (4,4'-bis[N-(1-naphthyl)-N-phenylamino]biphenyl), triphenyl-amine derivative (e.g., m-MTDATA (4,4',4"-tris(3-methyl-phenylphenylamino)triphenylamine)), polyvinylcarbazole and poly(3,4-ethylenedioxythiophene). Such a hole transport material may be used alone or may be used by mixing or stacking it with a different hole transport material. The thickness of the hole transport layer varies depending on the electrical conductivity of the hole transport layer and cannot be indiscriminately specified, but is preferably from 10 nm to 10 μm, more preferably from 10 nm to 1 μm.

The electron transport material constituting the electron transport layer is not particularly limited, but known electron transport materials can be used, such as quinolinol derivative metal complex (e.g., $Alq_3$ (aluminum trisquinolinolate)), oxadiazole derivative and triazole derivative. Such an electron transport material may be used alone or may be used by mixing or stacking it with a different electron transport material. The thickness of the electron transport layer varies depending on the electrical conductivity of the electron transport layer and cannot be indiscriminately specified, but is preferably from 10 nm to 10 μm, more preferably from 10 nm to 1 μm.

These light-emitting materials, hole transport materials and electron transport materials for use in respective layers each may be used alone for forming each layer or may be used by mixing it with a material having a different function. Each layer may also be formed by using a polymer material as the binder. The polymer material used for this purpose is not particularly limited but examples thereof include polymethyl methacrylate, polycarbonate, polyester, polysulfone and polyphenylene oxide.

The method for the film formation of the light-emitting material, hole transport material and electron transport material used in respective layers is not particularly limited, but a resistance heating vapor deposition method, an electron beam vapor deposition method, a sputtering method, a coating method, a solution coating method and the like can be used. In the case of a low molecular compound, resistance heating vapor deposition and electron beam vapor deposition are mainly used and in the case of a polymer material, a coating method is mainly used.

The anode material used for the organic light-emitting element of the present invention is not particularly limited, but known transparent electrically conducting materials can be used, such as electrically conducting polymer (e.g., ITO (indium tin oxide), tin oxide, zinc oxide, polythiophene, polypyrrole, polyaniline). The surface resistance of the electrode formed of this transparent electrically conducting material is preferably from 1 to 50 Ω/□ (ohm/square). The method for the film formation of this anode material is not particularly limited, but an electron beam vapor deposition method, a sputtering method, a chemical reaction method, a coating method and the like can be used. The thickness of the anode is preferably from 50 to 300 nm.

For the purpose of mitigating the injection barrier against injection of holes, a buffer layer may be inserted between the anode and the hole transport layer or an organic layer stacked adjacently to the anode. The material constituting the buffer layer is not particularly limited, but known materials such as copper phthalocyanine are used.

The cathode material used in the organic light-emitting element of the present invention is not particularly limited, but known cathode materials can be used, such as Al, MgAg alloy, alkali metal (e.g., Li, Cs), alkaline earth metal (e.g., Ca, Ba) and alloy of Al and alkali metal (e.g., AlCa). The method for the film formation of this cathode material is not particularly limited, but a resistance heating vapor deposition method, an electron beam vapor deposition method, a sputtering method, an ion plating method and the like can be used. The thickness of the cathode is preferably from 10 nm to 1 μm, more preferably from 50 to 500 nm. However, in the case where a highly active metal such as alkali metal and alkaline earth metal is used as the cathode, the thickness of the cathode is preferably from 0.1 to 100 nm, more preferably from 0.5 to 50 nm. Also, in this case, a metal layer stable against air is further stacked on the cathode for the purpose of protecting the cathode metal. Examples of the metal used for this purpose include Al, Ag, Au, Pt, Cu, Ni and Cr. The thickness of the metal layer is preferably from 10 nm to 1 μm, more preferably from 50 to 500 nm.

For the purpose of enhancing the electron injection efficiency, an insulating layer having a thickness of 0.1 to 10 nm may be inserted between the cathode and the electron transport layer or an organic layer stacked adjacently to the cathode. The insulating layer is not particularly limited, but known cathode materials such as lithium fluoride, magnesium fluoride, magnesium oxide and alumina can be used.

Furthermore, a hole block layer may also be provided adjacently to the cathode side of the light-emitting layer for the purpose of suppressing the passing of holes through the light-emitting layer and efficiently recombining holes with electrons in the light-emitting layer.

For the substrate used in the organic polymer light-emitting element of the present invention, an insulating substrate transparent to light emission wavelength of the light-emitting material can be used. The transparent insulating substrate is not particularly limited, but glass and other known materials including transparent plastics such as PET (polyethylene terephthalate) and polycarbonate can be used.

The organic polymer light-emitting element of the present invention can be used to constitute a picture element in a matrix or segment system by a known method or may be used as a backlight without forming a picture element.

BEST MODE FOR CARRYING OUT THE INVENTION

The present invention is described in greater detail below by referring to representative Examples, however, the present invention should not be construed as being limited thereto. The organic polymer light-emitting element material of the present invention is a polymer material, but since the same process was used for the polymerization of the polymerizable composition containing a polymerizable gold complex, synthesis examples of polymerizable gold complexes are first described and synthesis examples of polymers using these compounds are then described together.

The devices used for the analysis in the following Examples are shown below. Unless otherwise indicated, the reagents were a commercial product (guaranteed) used without purification.
1) Elemental Analyzer
   Model CHNS-932, manufactured by LECO Corporation
2) GPC Measurement (Measurement of Molecular Weight)
   Column: Shodex KF-G+KF804L+KF802+KF801
   Eluent: tetrahydrofuran (THF)
   Temperature: 40° C.
   Detector: RI (Shodex RI-71)

3) ICP Elemental Analysis
   ICPS 8000, manufactured by Shimadzu Corporation

EXAMPLE 1

Synthesis of Polymerizable Gold Complex (1)

Polymerizable Gold Complex (1) was synthesized by reacting sodium tetrachloroaurate (III) with thiodiglycol and then with bis(diphenylphosphino)methane having a polymerizable functional group. More specifically, 20 ml of tetrahydrofuran (hereinafter simply referred to as "THF") was added to 2.0 g (5.2 mmol) of bis(diphenylphosphino)-methane and while cooling on ice, 3.5 ml (5.6 mmol) of a 1.6M hexane solution of n-butyl lithium was added dropwise. After adding the THF solution containing 10 mg (0.05 mmol) of Lithium tetrachlorocuprate to the resulting slurry, a 10 ml THF solution containing 0.85 g (5.6 mmol) of 4-vinylbenzyl chloride was added dropwise and stirred at room temperature for 3 hours. Thereafter, the solvent was removed by distillation under reduced pressure and the organic material was extracted with dichloromethane and then dried under reduced pressure. The obtained solid was purified by silica gel column chromatography (eluate: dichloromethane) and dried under reduced pressure to obtain 1.2 g (2.4 mmol) of Compound (A) as a colorless solid.

Separately, a water (5 ml)-methanol (7.5 ml) solution containing 0.40 g (1.0 mmol) of sodium tetrachloroaurate (III) dihydrate was cooled on ice and thereto, a 5 ml methanol solution containing 0.37 g (3.0 mmol) of thiodiglycol was added. To the resulting solution, a chloroform (5 ml)-methanol (5 ml) solution containing 0.25 g (0.50 mmol) of Compound (A) was added and stirred at room temperature for 2 hours. The produced colorless precipitate was collected by filtration, washed with methanol and dried under reduced pressure. The obtained colorless solid was recrystallized from a dichloromethane-methanol mixed solution to obtain 0.25 g (0.33 mmol) of the objective Polymerizable Gold Complex

(1) as a colorless solid. The identification was performed by CHN elemental analysis and mass spectrometry.

Elemental analysis:

| | | |
|---|---|---|
| Calculated (as $C_{34}H_{30}AuCl_2P_2$) | C 42.30, | H 3.13 |
| Found | C 42.57, | H 3.10 |
| Mass spectrometry (FAB+) | 964 ($M^+$) | |

EXAMPLE 2

Synthesis of Polymerizable Gold Complex (2)

Polymerizable Gold Complex (2) was synthesized by the reaction of Polymerizable Gold Complex (1) and bis(diphenylphosphino)methane. More specifically, 150 mg (0.20 mmol) of Gold Complex (1) was dissolved in 10 ml of dichloromethane and thereto, 77 mg (0.20 mmol) of bis(diphenylphosphino)methane and 100 mg (0.39 mmol) of silver trifluoromethanesulfonate were added and stirred at room temperature for 2 hours. After removing the solvent by distillation under reduced pressure, the obtained reaction mixture was extracted with dichloromethane and then dried under reduced pressure. The residue was dissolved in a small amount of dichloromethane and after further adding methanol, concentrated and the obtained crystal was collected by filtration and dried to obtain 118 mg (0.096 mmol) of the objective Polymerizable Gold Complex (2). The identification was performed by CHN elemental analysis and mass spectrometry.

Elemental analysis:

| | | |
|---|---|---|
| Calculated (as $C_{61}H_{52}Au_2F_6O_6P_4S_2$) | C 46.46, | H 3.32 |
| Found | C 46.83, | H 3.59 |
| Mass spectrometry (FAB+) | 639 ($M^+$) | |

EXAMPLE 3

Synthesis of Polymerizable Gold Complex (3-1)

Polymerizable Gold Complex (3-1) was synthesized by reacting the gold complex obtained by the reaction between sodium tetrachloroaurate (III) and triphenylphosphine having a polymerizable functional group, with phenylbutadiyne synthesized by a known method (see, P. Cadiot and W. Chodkiewicz, *Chemistry of Acetylenes*, H. G. Viehe, ed., Marcel Dekker, New York (1969)). More specifically, 20 ml of dried THF was added to 341 mg (14 mmol) of magnesium and thereto, a 10 ml THF solution containing 2.70 g (15 mmol) of 4-bromostyrene was added dropwise to prepare a Grignard reagent. To the resulting solution, a 10 ml THF solution containing 2.50 g (11 mmol) of chlorodiphenylphosphine was added dropwise and stirred at room temperature of 1.5 hours. After removing the solvent by distillation under reduced pressure, the residue was purified by silica gel column chromatography and recrystallized from a hexane solution to obtain 2.30 g (8.3 mmol) of (4-vinylphenyl)diphenylphosphine Compound (B).

Subsequently, 250 mg (0.63 mmol) of sodium tetrachloroaurate (III) dihydrate was dissolved in a mixed solvent containing 2.5 ml of acetone and 2.5 ml of ethanol and thereto, a 5 ml chloroform solution containing 360 mg (1.25 mmol) of Compound (B) was added and stirred at room temperature for 15 minutes. The produced precipitate was separated by filtration through a glass filter and the obtained solution was cooled to −20° C. to obtain 254 mg (0.49 mmol) of Gold Complex (C).

Then, 100 mg (0.19 mmol) of Gold Complex (C) was suspended in 5 ml of methanol and thereto, 30 mg (0.24 mmol) of phenylbutadiyne and 15 mg (0.28 mmol) of sodium methoxide were added and stirred at room temperature for 16 hours. After removing the solvent by distillation under reduced pressure, a small amount of diethyl ether was added and the resulting solution was passed through a glass filter. The solvent was again removed by distillation under reduced pressure from the obtained solution and the residue was purified by silica gel column chromatography and dried under reduced pressure to obtain 79 mg (0.13 mmol) of the objective Polymerizable Gold Complex (3-1). The identification was performed by CHN elemental analysis and mass spectrometry.

Elemental analysis:

| Calculated (as $C_{30}H_{22}AuP$) | C 59.03, | H 3.63 |
|---|---|---|
| Found | C 58.88, | H 3.59 |
| Mass spectrometry (FAB+) | 610 ($M^+$) | |

EXAMPLE 4

Synthesis of Polymerizable Gold Complex (3-2)

(3-2)

Polymerizable Gold Complex (3-2) was synthesized by the same manner as the synthesis of polymerizable gold complex (3-1) except using 4-(4-bromobuthyl)styrene instead of 4-bromostyrene, chlorodiethylphosphine instead of chlorodiphenylphosphine and 1-ethynylnaphthalene instead of phenylbutadiyne. The identification was performed by CHN elemental analysis and mass spectrometry.

Elemental analysis:

Calculated (as $C_{28}H_{32}AuP$): C, 56.38; H, 5.41;

Found: C, 55.91; H, 5.76.

Mass spectrometry (FAB+): 596 ($M^+$)

EXAMPLE 5

Synthesis of Polymerizable Gold Complex (4-1)

(1)

(4-1)

Polymerizable Gold Complex (4-1) was synthesized by the reaction of Polymerizable Gold Complex (1) and phenylacetylene. More specifically, 103 mg (0.11 mmol) of Polymerizable Gold Complex (1) was suspended in 5 ml of methanol and thereto, 25 mg (0.24 mmol) of phenylacetylene and 15 mg (0.28 mmol) of sodium methoxide were added and stirred at room temperature for 24 hours. After removing the solvent by distillation under reduced pressure, a small amount of diethyl ether was added and the resulting solution was passed through a glass filter. The solvent was again removed by distillation under reduced pressure from the obtained solution and the residue was purified by silica gel column chromatography and dried under reduced pressure to obtain 60 mg (0.055 mmol) of the objective Polymerizable Gold Complex (4-1). The identification was performed by CHN elemental analysis and mass spectrometry.

Elemental analysis:

| Calculated (as $C_{50}H_{40}Au_2P_2$) | C 54.76, | H 3.68 |
|---|---|---|
| Found | C 55.02, | H 3.55 |
| Mass spectrometry (FAB+) | 1096 ($M^+$) | |

EXAMPLE 6 TO 9

Synthesis of Polymerizable Gold Complex (4-2) to (4-5)

Each of Polymerizable Gold Complex (4-2) to (4-5) was synthesized by the same manner as the synthesis of polymerizable gold complex (4-1) except using alkyne instead of phenylacetylene.

TABLE 1

| Example | Compound | $R^{101}$ | n | $C_{obs}$ ($C_{calcd}$) | $H_{obs}$ ($H_{calcd}$) | Mass Spectrometry Value |
|---|---|---|---|---|---|---|
| 6 | (4-2) | $C_6H_4$—$C_6H_5$ | 1 | 59.62 (59.83) | 3.87 (3.55) | 1248 ($M^+$) |
| 7 | (4-3) | $C_6H_4$—OMe | 2 | 55.83 (55.61) | 3.68 (3.19) | 1204 ($M^+$) |
| 8 | (4-4) | COOMe | 1 | 47.56 (47.49) | 3.42 (3.07) | 1060 ($M^+$) |
| 9 | (4-5) | t-Bu | 2 | 54.36 (54.58) | 4.38 (4.75) | 1104 ($M^+$) |

EXAMPLE 10

Synthesis of Polymerizable Gold Complex (5-1)

Polymerizable Gold Complex (5-1) was synthesized by reacting Gold Complex (C) having a polymerizable functional group with bis(trimethylsilyl)octatetrayne synthesized by a known method (see, P. Cadiot and W. Chodkiewicz, *Chemistry of Acetylenes*, H. G. Viehe, ed., Marcel Dekker, New York (1969)). More specifically, 98 mg (0.19 mmol) of Gold Complex (C) was suspended in 10 ml of methanol and thereto, 14 mg (0.26 mmol) of sodium methoxide and 24 mg (0.099 mmol) of bis(trimethylsilyl)octatetrayne were added and stirred at room temperature for 8 hours. The purified brown precipitate was collected by filtration through a glass filter, washed with methanol and dried under reduced pressure to obtain 49 mg (0.046 mmol) of the objective Polymerizable Gold Complex (5-1). The identification was performed by CHN elemental analysis and mass spectrometry.

Elemental analysis:

| Calculated (as $C_{48}H_{34}Au_2P_2$) | C 54.05, | H 3.21 |
|---|---|---|
| Found | C 54.47, | H 3.03 |
| Mass spectrometry (FAB+) | 1066 ($M^+$) | |

EXAMPLE 11

Synthesis of Polymerizable Gold Complex (5-2)

(D)

-continued (5-2)

Polymerizable Gold Complex (5-2) was synthesized by the same manner as the synthesis of polymerizable gold complex (5-1) except using Polymerizable Gold Complex (D) synthesized in the Example 4 instead of Gold Complex (C) having a polymerizable functional group and bis(trimethylsilyl) butadiyne instead of bis(trimethylsilyl)-octatetrayne. The identification was performed by CHN elemental analysis and mass spectrometry.

Elemental analysis:

| | | |
|---|---|---|
| Calculated (as $C_{36}H_{50}Au_2P_2$) | C 46.06, | H 5.37 |
| Found | C 45.71, | H 5.80 |
| Mass spectrometry (FAB+) | 938 (M⁺) | |

EXAMPLE 12

Synthesis of Polymerizable Gold Complex (6-1)

Polymerizable Gold Complex (6-1) was synthesized by the reaction of Polymerizable Gold Complex (1) and 1,3-propanedithiol. More specifically, 131 mg (0.14 mmol) of Polymerizable Gold Complex (1) was dissolved in 10 ml of dichloromethane and thereto, a 2 ml ethanol solution containing 15 mg (0.14 mmol) of 1,3-propanedithiol and 17 mg (0.28 mmol) of ethanolamine was added and stirred at room temperature for 2 hours. After removing the solvent by distillation under reduced pressure, the obtained reaction mixture was recrystallized from a chloroform-methanol mixed solvent to obtain 75 mg (0.075 mmol) of the objective Polymerizable Gold Complex (6-1) as a pale yellow solid. The identification was performed by CHN elemental analysis and mass spectrometry.

Elemental analysis:

| | | |
|---|---|---|
| Calculated (as $C_{37}H_{36}Au_2P_2S_2$) | C 44.41, | H 3.63 |
| Found | C 44.25, | H 3.88 |
| Mass spectrometry (FAB+) | 1000 (M⁺) | |

EXAMPLE 13

Synthesis of Polymerizable Gold Complex (6-2)

(6-2)

Polymerizable Gold Complex (6-2) was synthesized by the same manner as the synthesis of polymerizable gold complex (6-1) except using benzenethiol instead of 1,3-propanedithiol. The identification was performed by CHN elemental analysis and mass spectrometry.

Elemental analysis:

| | | |
|---|---|---|
| Calculated (as $C_{46}H_{40}Au_2P_2S_2$) | C 49.65, | H 3.62 |
| Found | C 49.23, | H 3.29 |
| Mass spectrometry (FAB+) | 1112 (M⁺) | |

EXAMPLE 14

Synthesis of Polymerizable Gold Complex (7)

(7)

Polymerizable Gold Complex (7) was synthesized by the reaction between chloro(triphenylphosphine) gold (I) synthesized by a known method (see, C. A. McAuliffe et al., *J. Chem. Soc., Dalton Trans.*, 1730 (1979)) and 4-(trimethylsilylethynyl)styrene synthesized by a known method (see, A. Hirao et al., *Macromolecules*, 26, 6985 (1993)). More specifically, 100 mg (0.20 mmol) of chloro(triphenyl-phosphine) gold (I) was suspended in 5 ml of methanol and thereto, 45 mg (0.22 mmol) of 4-(trimethylsilylethynyl)-styrene and 15 mg (0.28 mmol) of sodium methoxide were added and stirred at room temperature for 24 hours. After removing the solvent by distillation under reduced pressure, a small amount of diethyl ether was added and the resulting solution was passed through a glass filter. The solvent was again removed by distillation under reduced pressure from the obtained solution and the residue was purified by silica gel column chromatography and dried under reduced pressure to obtain 72 mg (0.12 mmol) of the objective Polymerizable Gold Complex (7). The identification was performed by CHN elemental analysis and mass spectrometry.

Elemental analysis:

| | | |
|---|---|---|
| Calculated (as $C_{28}H_2AuP$) | C 57.35, | H 3.78 |
| Found | C 56.94, | H 3.45 |
| Mass spectrometry (FAB+) | 586 ($M^+$) | |

EXAMPLE 15

Synthesis of Polymerizable Gold Complex (8)

(8)

Polymerizable Gold Complex (8) was synthesized by reacting a gold complex obtained by the reaction between sodium tetrachloroaurate (III) and thiodiglycol, with 4-vinylbenzenethiol synthesized by a known method (see, Y. Choji et al., *Macromolecules*, 32, 7732 (1999)). More specifically, a water (5 ml)-methanol (7.5 ml) solution containing 600 mg (1.5 mmol) of sodium tetrachloroaurate (III) dihydrate was cooled on ice and thereto, a 5 ml methanol solution containing 0.55 g (4.5 mmol) of thiodiglycol was added. To this solution, a chloroform (5 ml)-methanol (5 ml) solution containing 288 mg (0.75 mmol) of bis(diphenylphosphino)methane was added and stirred at room temperature for 2 hours. The produced colorless precipitate was collected by filtration, washed with methanol and dried under reduced pressure. The obtained colorless solid was dissolved in 15 ml of dichloromethane and thereto, a 2 ml ethanol solution containing 79 mg (0.58 mmol) of 4-vinylbenzenethiol and 35 mg (0.58 mmol) of ethanolamine was added and stirred at room temperature for 2 hours. After removing the solvent by distillation under reduced pressure, the obtained reaction mixture was re-dissolved in ethanol and then filtered. The solvent was again removed by distillation under reduced pressure from the obtained filtrate and the residue was recrystallized from a chloroform-methanol mixed solution to obtain 175 mg (0.17 mmol) of the objective Polymerizable Gold Complex (8). The identification was performed by CHN elemental analysis and mass spectrometry.

Elemental analysis:

| | | |
|---|---|---|
| Calculated (as $C_{41}H_{36}Au_2P_2S_2$) | C 46.96, | H 3.46 |
| Found | C 47.22, | H 3.44 |
| Mass spectrometry (FAB+) | 1048 ($M^+$) | |

EXAMPLES 16 TO 30

Synthesis of Polymerizable Gold Complex-N-Vinylcarbazole Copolymer

Polymerizable Gold Complexes (1) to (8) were copolymerized with N-vinylcarbazole to synthesize Polymers (9) to (23), respectively, each having a light-emitting function and a hole transporting function and useful as the organic light-emitting element material. More specifically, 1.55 g (8.0 mmol) of N-vinylcarbazole, 0.080 mmol of the polymerizable gold complex and 13 mg (0.080 mmol) of AIBN were dissolved in 40 ml of dried toluene and an argon was blown thereinto for 1 hour. The temperature of the resulting solution was elevated to 80° C. to start the polymerization reaction and the solution was stirred as it is for 8 hours. After cooling to room temperature, the reaction solution was added dropwise to 250 ml of methanol to precipitate the polymerization product. The polymerization product was recovered by filtration and then dissolved in 25 ml of chloroform. The resulting solution was purified by adding dropwise and re-precipitating it in 250 ml of methanol and then dried in vacuum at 60° C. for 12 hours to obtain the objective copolymer. The recovery, average molecular weight, molecular weight distribution and gold complex content are shown in Table 2.

TABLE 2

| Example | Polymerizable Gold Complex | Polymer | Recovery (%) | Mn | Mw | Mn/Mw | Gold Complex Content (mol %) |
|---|---|---|---|---|---|---|---|
| 16 | (1) | 9 | 68 | 6300 | 14100 | 2.24 | 1.04 |
| 17 | (2) | 10 | 65 | 6900 | 18800 | 2.72 | 0.56 |
| 18 | (3)-1 | 11 | 72 | 4500 | 9600 | 2.13 | 0.91 |
| 19 | (3)-2 | 12 | 66 | 8500 | 20700 | 2.44 | 0.89 |
| 20 | (4)-1 | 13 | 75 | 5900 | 14100 | 2.39 | 1.04 |
| 21 | (4)-2 | 14 | 61 | 7000 | 16800 | 2.40 | 0.77 |
| 22 | (4)-3 | 15 | 70 | 7500 | 15500 | 2.07 | 0.81 |
| 23 | (4)-4 | 16 | 68 | 8100 | 17900 | 2.21 | 0.79 |
| 24 | (4)-5 | 17 | 65 | 6500 | 18000 | 2.77 | 0.65 |
| 25 | (5)-1 | 18 | 47 | 12100 | 31000 | 2.56 | 1.11 |
| 26 | (5)-2 | 19 | 52 | 11600 | 40300 | 3.47 | 1.20 |
| 27 | (6)-1 | 20 | 70 | 4100 | 14900 | 3.63 | 0.89 |
| 28 | (6)-2 | 21 | 68 | 6500 | 14100 | 2.17 | 0.90 |
| 29 | (7) | 22 | 42 | 6500 | 16200 | 2.49 | 1.18 |
| 30 | (8) | 23 | 51 | 20400 | 48800 | 2.39 | 1.07 |

Mn: number average molecular weight
Mw: weight average molecular weight

EXAMPLES 31 TO 33

Production and Evaluation of Organic Polymer Light-Emitting Element

Organic polymer light-emitting elements were produced by using an ITO (indium tin oxide)-attached substrate (produced by Nippo Electric Co., Ltd.) where two 4 mm-width ITO electrodes working out to the anode were formed like stripes on one surface of a 25 mm-square glass substrate. On the ITO (anode) of the ITO-attached substrate, poly(3,4-ethylenedioxythiophene).polystyrenesulfonic acid ("Baytron P", trade name, produced by Bayer AG) was coated by spin coating under the conditions of rotation number of 3,500 rpm and coating time of 40 seconds and then dried at 60° C. for 2 hours under reduced pressure in a vacuum dryer to form an anode buffer layer. The thickness of the obtained anode buffer layer was about 50 nm. Subsequently, a coating solution for forming a layer containing a light-emitting material and an electron transport material was prepared. That is, 21.0 mg of the light-emitting material shown in Table 3 and 9.0 mg of 2-(4-biphenyl)-5-(4-tert-butylphenyl)-1,3,4-oxadiazole (PBD) (produced by Tokyo Kasei Kogyo Co., Ltd.) as the electron transport material were dissolved in 2,970 mg of chloroform (produced by Wako Pure Chemical Industries, Ltd., guaranteed) and the resulting solution was filtered through a filter having a pore size of 0.2 µm to prepare the coating solution. The thus-prepared coating solution was coated on the anode buffer layer by spin coating under the conditions of rotation number of 3,000 rpm and coating time of 30 seconds and then dried at room temperature (25° C.) for 30 minutes to form a layer containing a light-emitting material and an electron transport material. The thickness of the obtained layer containing a light-emitting material and an electron transport material was about 100 nm. Thereafter, the substrate having formed thereon the layer containing a light-emitting material and an electron transport material was placed in a vapor deposition apparatus and calcium and aluminum were vapor co-deposited at a weight ratio of 1:10 to form two 3 mm-width cathodes arrayed like stripes and running in orthogonal to the extending direction of anodes. The thickness of the cathode obtained was about 50 nm. Finally, the anode and the cathode each was connected with a lead wire (wiring) in an argon atmosphere. In this way, 4 units of an organic polymer light-emitting element in a size of 4 mm (length)×3 mm (width) were produced. By using programmable D.C. voltage/current source TR6143 manufactured by Advantest Corp., a voltage was applied to the obtained organic EL element to cause light emission and the brightness of light emitted was measured by means of brightness meter BM-8 manufactured by Topcon Corp. The results of light emission color and initial brightness at 15 V are shown in Table 3 (the value shown is an average of 4 units of the element using each light-emitting material).

TABLE 3

| Example | Polymer | Light Emission Color | Initial Brightness at 15 V (cd/m²) |
|---|---|---|---|
| 31 | 11 | blue | 35 |
| 32 | 18 | red | 20 |
| 33 | 20 | green | 65 |

INDUSTRIAL APPLICABILITY

By virtue of the organic polymer light-emitting element using a phosphorescent material of the present invention, not only visible light from blue to red can be emitted with high efficiency but also the production of a large-area element by coating can be facilitated.

The invention claimed is:

1. An organic polymer light-emitting element material having a gold complex structure as a part of a side chain, which is obtained by polymerizing a composition containing a polymerizable gold complex represented by formula (5) or (9):

(5)

wherein $R^{12}$ represents a hydrogen atom, a cyano group, a silyl group having 3 to 20 carbon atoms, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an aryl group having 6 to 15 carbon atoms which may have a substituent, a heteroaryl group having 3 to 15 carbon atoms which may have a substituent, an acyl group having 1 to 15 carbon atoms, a carboxyl group, or an alkoxy carbonyl group having 2 to 15 carbon atoms, $R^{13}$ to $R^{15}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, and n represents an integer of 1 to 5, provided that at least one of $R^{12}$ to $R^{15}$ has a polymerizable functional group;

(9)

wherein $R^{21}$ to $R^{26}$ each independently represents a hydrogen atom, an alkyl group having 1 to 15 carbon atoms which may have a substituent, an alkyl group having 3 to 15 carbon atoms which has a cyclic structure and which may have a substituent, an alkenyl group having 2 to 15 carbon atoms which may have a substituent, an alkoxy group having 1 to 15 carbon atoms which may have a substituent, an aryl group having 6 to 15 carbon atoms which may have a substituent, a heteroaryl group having 3 to 15 carbon atoms which may have a substituent or an aryloxy group having 6 to 15 carbon atoms which may have a substituent, and n represents an integer of 1 to 5, provided that at least one of $R^{21}$ to $R^{26}$ represents a polymerizable functional group, wherein the polymerizable functional group is an organic group having a carbon-carbon double bond.

2. An organic polymer light-emitting element comprising a pair of electrodes having interposed therebetween at least one layer comprising the organic polymer light-emitting element material described in claim 1.

3. An organic polymer light-emitting element comprising a pair of electrodes having interposed therebetween at least one layer each comprising one or more organic polymer light-emitting element material described in claim 1.

* * * * *